United States Patent
Kamakura et al.

(10) Patent No.: US 10,595,780 B2
(45) Date of Patent: Mar. 24, 2020

(54) WEARABLE BIOLOGICAL INFORMATION SENSING DEVICE

(71) Applicant: Seiko Epson Corporation, Tokyo (JP)

(72) Inventors: Tomoyuki Kamakura, Matsumoto (JP); Hideo Miyasaka, Okaya (JP); Yoshihiko Yokoyama, Chino (JP)

(73) Assignee: Seiko Epson Corporation (JP)

( * ) Notice: Subject to any disclaimer, the term of this patent is extended or adjusted under 35 U.S.C. 154(b) by 89 days.

(21) Appl. No.: 15/673,844

(22) Filed: Aug. 10, 2017

(65) Prior Publication Data

US 2018/0070878 A1 Mar. 15, 2018

(30) Foreign Application Priority Data

Sep. 13, 2016 (JP) .................. 2016-178570

(51) Int. Cl.
*A61B 5/00* (2006.01)
*A61B 5/01* (2006.01)
*A61B 5/021* (2006.01)
*A61B 5/024* (2006.01)
*A61B 5/0402* (2006.01)
*A61B 5/0488* (2006.01)

(52) U.S. Cl.
CPC .............. *A61B 5/6832* (2013.01); *A61B 5/01* (2013.01); *A61B 5/021* (2013.01); *A61B 5/02438* (2013.01); *A61B 5/0402* (2013.01); *A61B 5/0488* (2013.01); *A61B 2562/164* (2013.01)

(58) Field of Classification Search
CPC ....... A61B 5/01; A61B 5/6832; A61B 5/6833; A61B 5/021; A61B 5/02438; A61B 5/0402; A61B 5/0488; A61B 2562/164; H05K 1/147

USPC .......................................................... 600/300
See application file for complete search history.

(56) References Cited

U.S. PATENT DOCUMENTS

| | | | | |
|---|---|---|---|---|
| 3,930,506 A | * | 1/1976 | Overend | A61B 17/1322 606/203 |
| 4,067,342 A | * | 1/1978 | Burton | A61B 5/04087 607/148 |
| 4,259,965 A | * | 4/1981 | Fukuda | A61B 5/0408 600/392 |
| 5,154,690 A | * | 10/1992 | Shiono | A61F 5/0102 602/21 |

(Continued)

FOREIGN PATENT DOCUMENTS

| | | |
|---|---|---|
| JP | 2008-086399 A | 4/2008 |
| JP | 2016-021557 A | 2/2016 |

(Continued)

*Primary Examiner* — Carl H Layno
*Assistant Examiner* — Michael J Lau
(74) *Attorney, Agent, or Firm* — Harness, Dickey & Pierce, P.L.C.

(57) ABSTRACT

An electronic apparatus includes: a base; a functional element; and a first member and a second member which connect the base and the functional element to each other. The first member and the second member have different elastic moduli from each other. The elastic modulus of the first member is higher than the elastic modulus of the second member. At least a part of the first member is situated more closely to a center of the functional element than the second member, as viewed in a plan view taken from a direction in which the base and the functional element are arrayed.

8 Claims, 12 Drawing Sheets

(56) References Cited

U.S. PATENT DOCUMENTS

| | | | | |
|---|---|---|---|---|
| 5,323,650 A * | 6/1994 | Fullen | A61B 5/1036 | 340/573.1 |
| 5,467,771 A * | 11/1995 | Narimatsu | A61B 5/021 | 600/485 |
| 9,373,762 B2 | 6/2016 | Sawada et al. | | |
| 9,554,484 B2 * | 1/2017 | Rogers | A61B 5/01 | |
| 2004/0000195 A1 * | 1/2004 | Yanai | A61B 5/113 | 73/717 |
| 2007/0100219 A1 * | 5/2007 | Sweitzer | A61B 5/0002 | 600/323 |
| 2007/0129776 A1 * | 6/2007 | Robins | A61N 5/0613 | 607/88 |
| 2008/0257589 A1 * | 10/2008 | Ostmann | H05K 1/0271 | 174/254 |
| 2009/0076363 A1 * | 3/2009 | Bly | A61B 5/0205 | 600/372 |
| 2009/0203984 A1 * | 8/2009 | Dias | A41D 13/1281 | 600/388 |
| 2009/0283891 A1 * | 11/2009 | Dekker | H01L 23/5387 | 257/690 |
| 2010/0234715 A1 * | 9/2010 | Shin | A61B 5/0402 | 600/388 |
| 2010/0294552 A1 * | 11/2010 | Kobayashi | H01L 23/49827 | 174/260 |
| 2010/0304530 A1 * | 12/2010 | Yim | H01L 23/04 | 438/109 |
| 2011/0080713 A1 * | 4/2011 | Sunohara | H01L 23/147 | 361/760 |
| 2011/0319787 A1 * | 12/2011 | Lamoise | A61B 5/103 | 600/549 |
| 2012/0157804 A1 * | 6/2012 | Rogers | A61B 5/0422 | 600/345 |
| 2012/0246795 A1 * | 10/2012 | Scheffler | A41D 1/002 | 2/69 |
| 2013/0338746 A1 * | 12/2013 | Guvanasen | A61N 1/0502 | 607/116 |
| 2014/0303452 A1 * | 10/2014 | Ghaffari | A61B 1/05 | 600/301 |
| 2014/0340857 A1 * | 11/2014 | Hsu | H05K 1/0283 | 361/749 |
| 2015/0338293 A1 * | 11/2015 | Masunishi | G01L 1/22 | 73/649 |
| 2015/0364661 A1 * | 12/2015 | Sawada | H01L 33/54 | 257/98 |
| 2015/0380355 A1 * | 12/2015 | Rogers | H01L 23/538 | 257/773 |
| 2016/0015280 A1 * | 1/2016 | Hyde | G16H 50/30 | 600/301 |
| 2016/0027737 A1 * | 1/2016 | Rogers | H01L 23/5387 | 257/618 |
| 2016/0045135 A1 * | 2/2016 | Kim | A61B 5/04087 | 600/391 |
| 2016/0051195 A1 * | 2/2016 | Pang | A61B 5/6833 | 600/301 |
| 2016/0058380 A1 * | 3/2016 | Lee | A61B 5/14532 | 600/365 |
| 2016/0066854 A1 * | 3/2016 | Mei | A61B 5/6833 | 600/391 |
| 2016/0099517 A1 * | 4/2016 | Fernandes | H01R 12/79 | 439/39 |
| 2016/0120434 A1 * | 5/2016 | Park | A61B 5/6832 | 600/301 |
| 2016/0121098 A1 * | 5/2016 | Kockx | H01R 13/506 | 607/115 |
| 2016/0136882 A1 * | 5/2016 | Cobbett | B29C 65/7832 | 156/218 |
| 2016/0157779 A1 * | 6/2016 | Baxi | A61B 5/6831 | 600/301 |
| 2016/0183874 A1 * | 6/2016 | Takizawa | A61B 5/0404 | 600/391 |
| 2016/0256067 A1 * | 9/2016 | Low | A61B 5/04014 | |
| 2016/0256665 A1 * | 9/2016 | Doshi | F16M 13/022 | |
| 2017/0034907 A1 * | 2/2017 | Iwase | H05K 1/0283 | |
| 2017/0099730 A1 * | 4/2017 | Iwase | H05K 1/092 | |

FOREIGN PATENT DOCUMENTS

| | | |
|---|---|---|
| JP | 2016-178121 A | 10/2016 |
| JP | 2017-069530 A | 4/2017 |
| WO | WO-2013190748 A1 * | 12/2013 |

* cited by examiner

WEARABLE BIOLOGICAL INFORMATION SENSING DEVICE

BACKGROUND

1. Technical Field

The present invention relates to an electronic apparatus.

2. Related Art

For example, JP-A-2008-86399 discloses a configuration in which a myoelectric detection device for measuring a myoelectric activity state is installed on an arm of a living body with a device fastening strap. The device fastening strap includes a device fastener made up of a concave part recessed toward the side that does not come into contact with the body surface, and a strap to be wound around the arm. As the myoelectric detection device is fitted into the device fastener, the myoelectric detection device is fastened to the device fastening strap.

However, with the device fastening strap disclosed in JP-A-2008-86399, the myoelectric detection device is fastened to the device fastener. Therefore, when installed on the arm, the myoelectric detection device cannot follow the surface shape of the arm. Thus, it is difficult to bring the myoelectric detection device into sufficiently tight contact with the arm.

SUMMARY

An advantage of some aspects of the invention is to provide an electronic apparatus having a functional element that can easily follow the surface of a target object (for example, a living body).

The advantage can be achieved by the following configurations.

An electronic apparatus according to an aspect of the invention includes: a base; a functional element; and a first member and a second member which connect the base and the functional element to each other. The first member and the second member have different elastic moduli from each other.

With this configuration, since the first and second members become elastically deformed, the functional element can easily change attitude with respect to the base and the functional element can easily follow the surface of a target object (for example, a living body). Therefore, an electronic apparatus having a functional element that can easily follow the surface of a target object can be provided.

In the electronic apparatus according to the aspect of the invention, it is preferable that the elastic modulus of the first member is higher than the elastic modulus of the second member, and that at least a part of the first member is situated more closely to a center of the functional element than the second member, as viewed in a plan view taken from a direction in which the base and the functional element are arrayed.

With this configuration, the functional element can follow the surface of a target object more easily.

In the electronic apparatus according to the aspect of the invention, it is preferable that at least one of the first member and the second member has a gradient of the elastic modulus.

With this configuration, the functional element can follow the surface of a target object more easily.

It is preferable that the electronic apparatus according to the aspect of the invention further includes a third member which has elasticity and is arranged to cover at least apart of peripheries of the functional element, as viewed in a plan view taken from a direction in which the base and the functional element are arrayed.

With this configuration, the functional element can be protected.

In the electronic apparatus according to the aspect of the invention, it is preferable that the third member has an elastic modulus that is lower than the elastic modulus of the second member.

With this configuration, the third member can be restrained from making it difficult for the functional element to change attitude with respect to the base.

An electronic apparatus according to an aspect of the invention includes: a base; a functional element; and a first member and a second member which connect the base and the functional element to each other. The first member and the second member have different flexibilities from each other.

With this configuration, since the first and second members become elastically deformed, the functional element can easily change attitude with respect to the base and the functional element can easily follow the surface of a target object (for example, a living body). Therefore, an electronic apparatus having a functional element that can easily follow the surface of a target object can be provided.

In the electronic apparatus according to the aspect of the invention, it is preferable that the second member has electrical conductivity and that the functional element is electrically connected to the base via the second member.

With this configuration, apart of an electrical path can be formed by the second member and therefore the device can be simplified.

In the electronic apparatus according to the aspect of the invention, it is preferable that a plurality of the second members is arranged, spaced apart from each other.

With this configuration, a plurality of electrical paths can be formed by the second members.

In the electronic apparatus according to the aspect of the invention, it is preferable that the first member has an insulation property.

With this configuration, for example, in the case where a plurality of the second members is arranged, these second members can be restrained from forming a short circuit via the first member.

In the electronic apparatus according to the aspect of the invention, it is preferable that the first member or the second member includes air bubbles inside.

With this configuration, the first member or the second member can be deformed more easily.

In the electronic apparatus according to the aspect of the invention, it is preferable that the base has a flexible member which has flexibility and a hard member which is harder than the flexible member, and that the functional element is connected to the hard member via the first member and the second member.

With this configuration, the first and second members can be restrained from being stripped off the base as the base becomes deformed.

In the electronic apparatus according to the aspect of the invention, it is preferable that the functional element acquires biological information of the living body.

This configuration makes the electronic apparatus highly convenient.

It is preferable that the electronic apparatus according to the aspect of the invention is used in the state of being installed on the living body.

This configuration makes the electronic apparatus highly convenient.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, an electronic apparatus according to the invention will be described in detail, based on preferred embodiments shown in the accompanying drawings.

First Embodiment

Figure 1:
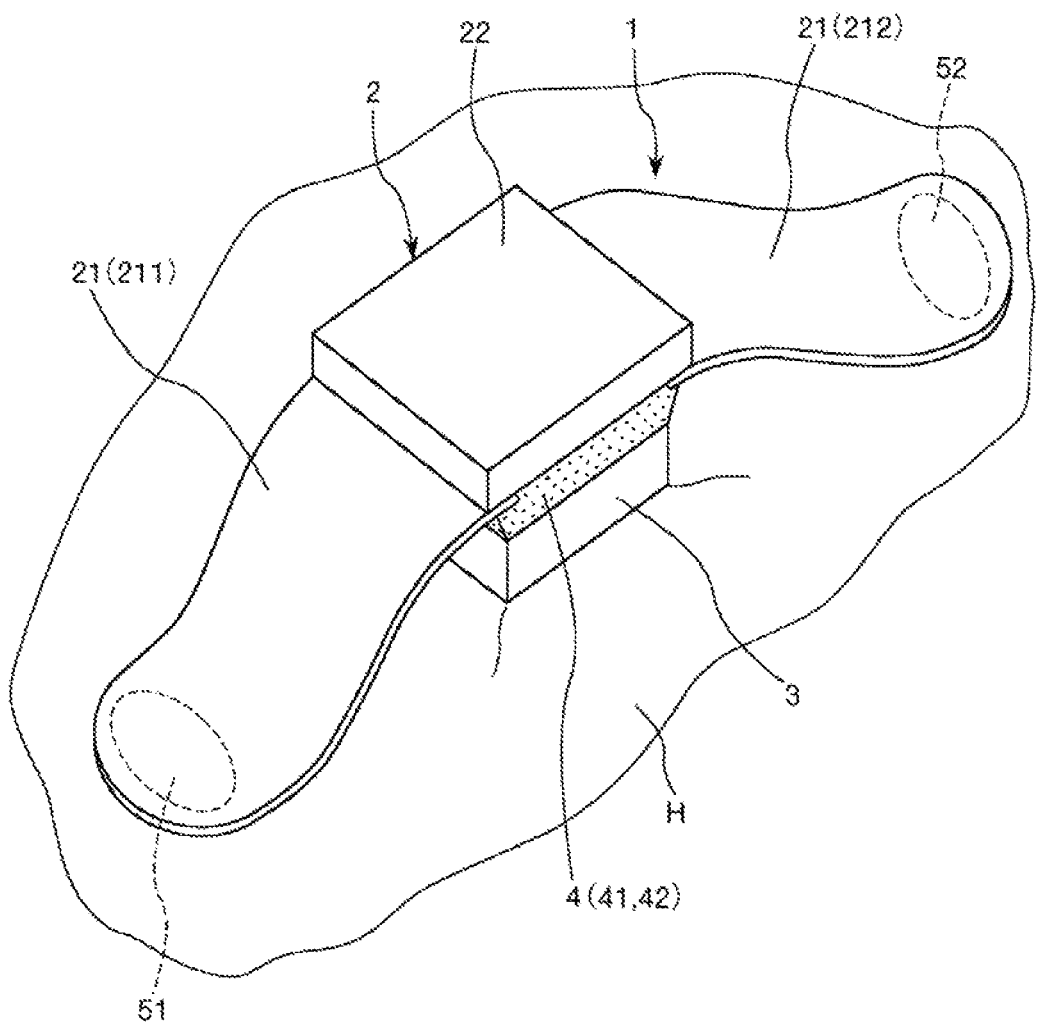
FIG. 1 is a perspective view of an electronic apparatus according to a first embodiment of the invention.
Figure 2:
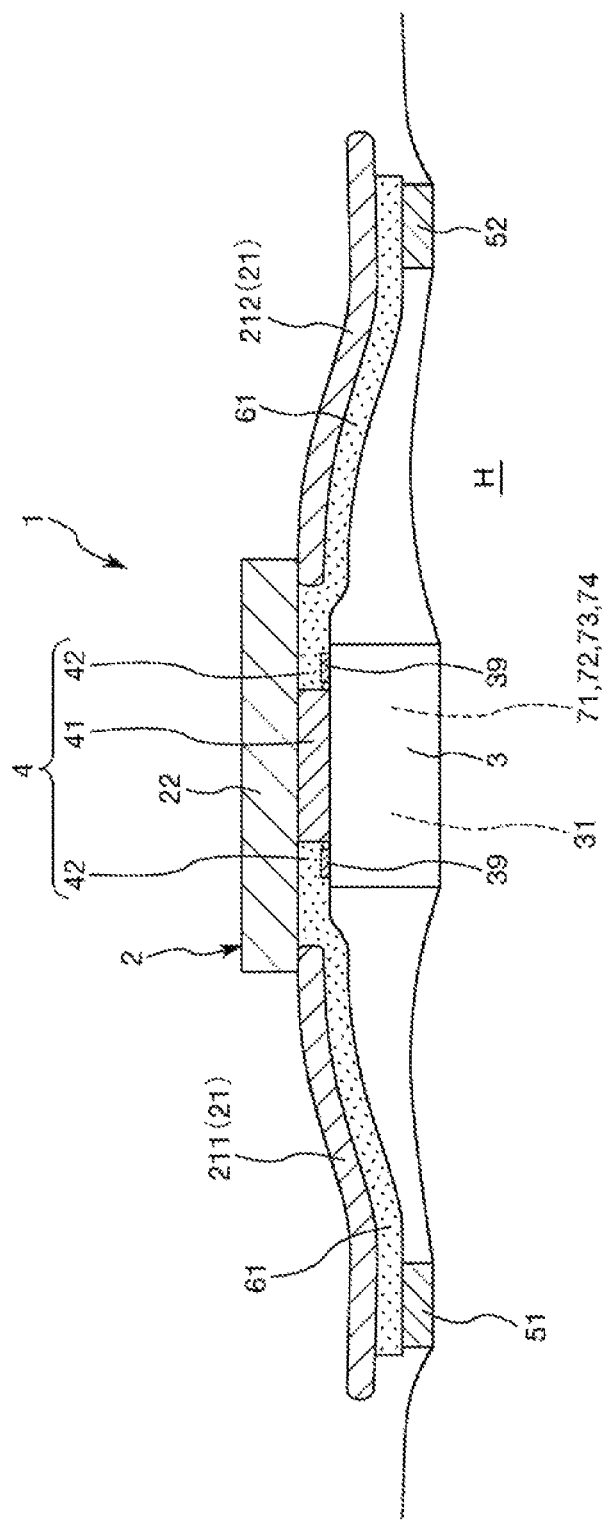
FIG. 2 is a cross-sectional view of the electronic apparatus shown in FIG. 1.
Figure 3:
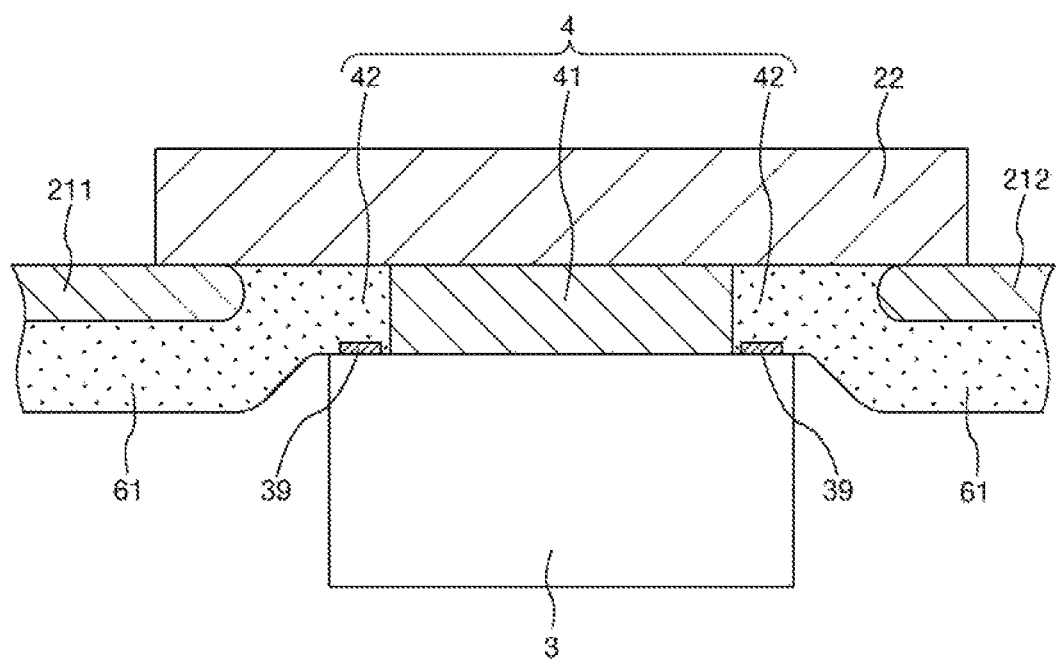
FIG. 3 is a cross-sectional view of the electronic apparatus shown in FIG. 1.
Figure 4:
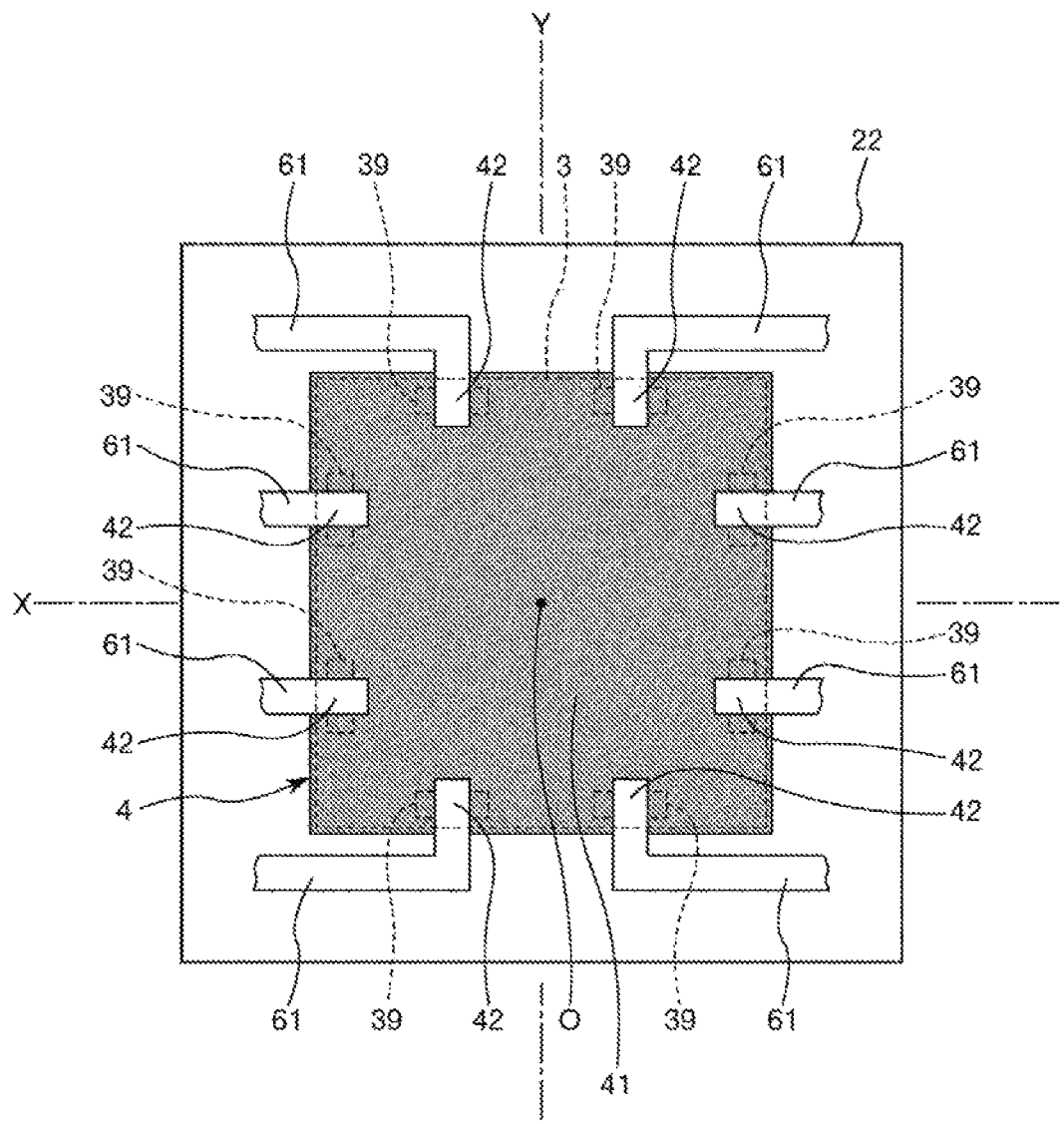
FIG. 4 is a plan view showing an adhesive layer of the electronic apparatus shown in FIG. 1.
Figure 5:
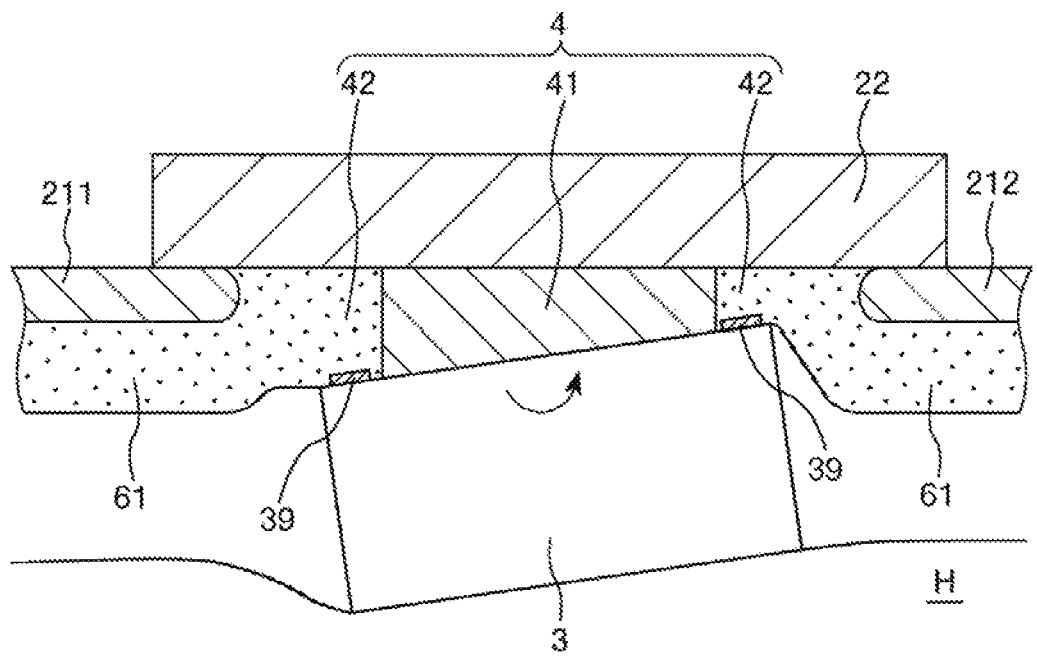
FIG. 5 is a cross-sectional view showing the displacement of a biological information acquirer with respect to a rigid substrate.
Figure 6:
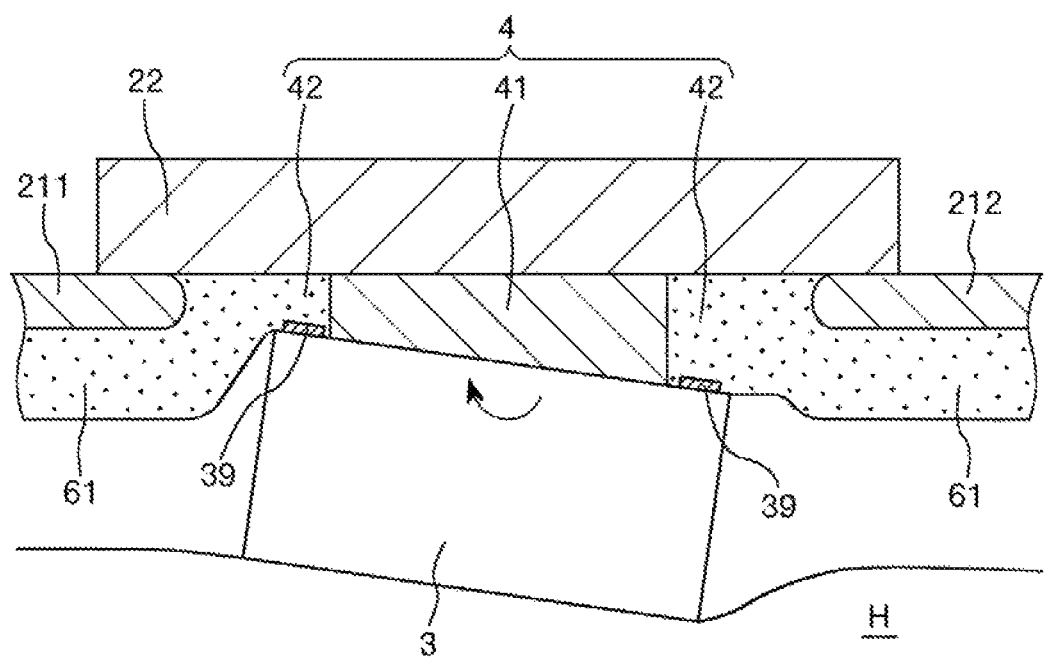
FIG. 6 is a cross-sectional view showing the displacement of the biological information acquirer with respect to the rigid substrate.

FIG. 1 is a perspective view of an electronic apparatus according to a first embodiment of the invention. FIGS. 2 and 3 are cross-sectional views of the electronic apparatus shown in FIG. 1. FIG. 4 is a plan view showing an adhesive layer of the electronic apparatus shown in FIG. 1. FIGS. 5 and 6 are cross-sectional views showing the displacement of a biological information acquirer with respect to a rigid substrate.

An electronic apparatus 1 shown in FIG. 1 is a wearable terminal for measuring biological information which is used in the state of being installed on a living body H (human) and which can acquire biological information (for example, electrocardiogram, electromyogram, body temperature, blood pressure, heart rate and the like) of the living body H. Such a configuration makes the electronic apparatus 1 highly convenient.

This electronic apparatus 1 includes a base 2, a biological information acquirer 3 as a functional element, and a first adhesive 41 as a first member and a second adhesive 42 as a second member which connect the base 2 and the biological information acquirer 3 to each other, as shown in FIG. 2. The first adhesive 41 and the second adhesive 42 have different elastic moduli from each other. In other words, the first adhesive 41 and the second adhesive 42 have different flexibilities from each other. With such a configuration, the first adhesive 41 and the second adhesive 42 become elastically deformed, thus allowing the biological information acquirer 3 to change attitude with respect to the base 2. Therefore, the biological information acquirer 3 can easily follow the surface (skin) of the living body H. Thus, the biological information acquirer 3 can be brought into sufficiently tight contact with the surface of the living body H, and biological information of the living body H can be acquired more accurately from the biological information acquirer 3. Particularly, since the first adhesive 41 and the second adhesive 42 have different elastic moduli from each other, the configuration of an adhesive layer 4 made up of the first adhesive 41 and the second adhesive 42 can be designed in a more sophisticated manner. Therefore, for example, the biological information acquirer 3 can follow the surface (skin) of the living body H more easily and the strength of the adhesive layer 4 can be increased. The "flexibility" can also be expressed by elastic modulus or degree of hardness. It can also be said that the first adhesive 41 and the second adhesive 42 have different elastic moduli from each other or have different degrees of hardness from each other. The elastic modulus in this case is, for example, Young's modulus, modulus of rigidity, Poisson's ratio, or ratio of volume change. The electronic apparatus 1 will be described in detail below.

As shown in FIG. 2, the electronic apparatus 1 has the base 2, the biological information acquirer 3, the adhesive layer 4, a part of which is situated between the base 2 and the biological information acquirer 3 and which connects these together, and a pair of electrode pads 51, 52 provided on the base 2. The electronic apparatus 1 is installed on the living body H, with the biological information acquirer 3 facing the side of the living body H. The base 2 has a viscous (sticky) bonding element, not illustrated, and this enables the base 2 to be bonded to the living body H. Hereinafter, the base 2, the biological information acquirer 3, the adhesive layer 4, and the electrode pads 51, 52 will be described in order.

The base 2 has a strap 21 as a flexible member having flexibility and a rigid substrate 22 as a hard member harder (having a higher Young's modulus) than the strap 21. The biological information acquirer 3 is connected to the rigid substrate 22 via the adhesive layer 4 (first adhesive 41 and second adhesive 42). Here, the rigid substrate 22 is hard enough to be hardly deformed (elastically deformed) by a stress within a range that is expected to occur during use. Since the biological information acquirer 3 is thus connected to the rigid substrate 22 via the adhesive layer 4, the separation of the adhesive layer 4 from the rigid substrate 22 can be restrained. For example, if a flexible or elastic substrate is used instead of the rigid substrate 22, the substrate expands and contracts in its planar direction or flexes in the direction of pressure and thus applies a stress to the joining surface between the substrate and the adhesive layer 4, posing the risk that the adhesive layer 4 may be separated from the substrate. In contrast, the use of the rigid substrate 22, which is hard and does not become substantially deformed, makes it difficult for the foregoing stress to be applied to the joining surface between the rigid substrate 22 and the adhesive layer 4. Therefore, a good joining state between the rigid substrate 22 and the adhesive layer 4 can be maintained and the separation of the adhesive layer 4 from the rigid substrate 22 can be restrained effectively.

Such a rigid substrate 22 is not particularly limited and may be hard or flexible, provided that the substrate is not elastic. For example, a glass epoxy substrate, glass composite substrate, ceramic substrate or the like as used in a printed wiring board, or a flexible polyimide film, PET film PEN film, LCP film, paper or the like can be used.

The strap 21 is flexible and elastic and can become deformed, expand, and contract, following the surface (skin) of the living body H when worn. Such a strap 21 includes two strap pieces 211, 212. The two strap pieces 211, 212 are connected to both side of the rigid substrate 22. The strap 21 (strap pieces 211, 212) is not particularly limited, provided that it is flexible and elastic. For example, various resin-based adhesives such as epoxy-based resin, acrylic-based resin, urethane-based resin or silicone-based resin, various rubber-based adhesives such as acrylic-based rubber, silicone-based rubber, butadiene-based rubber or styrene-based rubber, or thermoplastic elastomer or the like can be used. Also, adding a cellulose nanofiber, carbon nanofiber or the like reinforces the resin and makes a wire 61 hard to break. Although it is preferable that the strap 21 is both flexible and elastic as in the embodiment, it suffices that the strap 21 is at least flexible. As long as the strap 21 is flexible, the strap 21 can become deformed, following the surface of the living body H. In the case of the strap 21 that is not elastic, for example, a flexible substrate as used in a printed wiring board (insulating film-like substrate made of polyimide, polyester or the like) can be used as the strap 21.

Up to this point, the base 2 has been described. On such a base 2, a plurality of wires 61 is provided. These wires 61 are wires for electrically connecting the biological information acquirer 3 and the electrode pads 51, 52 to each other and have one end situated on the rigid substrate 22 and the other end situated at the free end of the strap 21 (end opposite to the rigid substrate 22).

Since the strap 21 is elastic, each wire 61 is elastic and configured not to break due to the expansion of the strap 21. Such wires 61 can be formed of, for example, a conductive resin material made up of various resin-based adhesives such as epoxy-based resin, acrylic-based resin, urethane-based resin or silicone-based resin, various rubber-based adhesives such as acrylic-based rubber, silicone-based rubber, butadiene-based rubber or styrene-based rubber, or various resin materials such as thermoplastic elastomer, mixed with various conductive fillers such as metal-based filler (for example, Au, Ag, Cu, Ni, Zn, Al), metal oxide-based filler (for example, $SnO_2$/Sb doped, $In_2O_3$/Sn doped, ZnO/Al doped), or carbon-based filler (for example, conductive carbon black, graphite). Particularly, it is preferable that each wire 61 is formed using a resin material with a lower Young's modulus than the strap 21. This makes the wires 61 more flexible and hard to break due to the expansion of the strap 21. Also, adding a cellulose nanofiber, carbon nanofiber or the like reinforces the resin and makes the wires 61 hard to break.

Of the pair of electrode pads 51, 52, one electrode pad 51 is arranged at the free end of the one strap piece 211 (end opposite to the rigid substrate 22) and electrically connected to the wires 61. Meanwhile, the other electrode pad 52 is arranged at the free end of the other strap piece 212 and electrically connected to the wires 61. These electrode pads 51, 52 are electrodes for acquiring an electrocardiogram of the living body H and electrically connected to the biological information acquirer 3 via the wires 61 and the second adhesive 42.

The biological information acquirer 3 can acquire biological information of the living body H. This makes the electronic apparatus 1 highly convenient. As the biological information, for example, electrocardiogram, electromyogram, body temperature, blood pressure, heart rate and the like may be employed. Of these, the biological information acquirer 3 in the embodiment can acquire information about electrocardiogram and body temperature. However, the types and number of items of biological information that can be acquired by the biological information acquirer 3 are not particularly limited and may be suitably set according to need.

The biological information acquirer 3 can acquire an electrocardiogram (flow of electricity in the heart) from between the electrode pads 51, 52. For example, the heart is situated slightly to the left of the center of the chest and is in the state of tilting laterally with the distal end of the heart (apex) facing down. The electricity in the heart flows from the sinus node situated in the upper right atrium of the heart toward the lower apex of the cardiac ventricle via the atrioventricular node situated substantially in the middle. Therefore, the electrical axis is in a bottom left diagonal direction. If the electrode pads 51, 52 are mounted in the same direction as this direction and on both sides of the heart, an electrocardiogram can be acquired from between these electrode pads 51, 52. The biological information acquirer 3 also has a thermosensitive element 31, for example, a thermistor, thermocouple, infrared temperature sensor or the like. With this thermosensitive element 31, the body temperature of the living body H can be detected.

Also, for example, a battery 71 as a power supply, an IC 72 as a control circuit, a storage 73 which stores acquired biological information (electrocardiographic waveforms and body temperature), a communicator 74 and the like are built in the biological information acquirer 3. The storage 73 is not particularly limited. For example, a flash memory or the like can be used. The communication measure of the communicator 74 is not particularly limited and may be wired or wireless. However, it is preferable to use wireless communication of, for example, Bluetooth (trademark registered) or the like.

Up to this point, the biological information acquirer 3 has been described. Next, the adhesive layer 4 connecting the biological information acquirer 3 to the rigid substrate 22 will be described. As shown in FIG. 3, the adhesive layer 4 has the first adhesive 41 and the second adhesive 42 arranged between the rigid substrate 22 and the biological information acquirer 3. The elastic modulus (Young's modulus) of the first adhesive 41 is higher than the elastic modulus (Young's modulus) of the second adhesive 42. As shown in FIG. 4, at least a part of the first adhesive 41 is situated more closely to the center O of the biological information acquirer 3 than the second adhesive 42, as viewed in a plan view taken from the direction in which the base 2 (rigid substrate 22) and the biological information acquirer 3 are arrayed (hereinafter also referred to simply as "as viewed in a plan view"). More specifically, the second adhesive 42 is arranged in such a way as to overlap an outer edge part of the biological information acquirer 3. The first adhesive 41 is arranged substantially in the entire area where the second adhesive 42 is arranged, of the area overlapping the biological information acquirer 3. Therefore, the first adhesive 41 has apart overlapping a center part of the biological information acquirer 3, as viewed in a plan view. It can be said that this part is situated more closely to the center O of the biological information acquirer 3 than the second adhesive 42. In the embodiment, the first adhesive 41 and the second adhesive 42 are provided in contact with each other and no substantial gap is formed between these. The first and second adhesives 41, 42 fill substantially the entire space held between the rigid substrate 22 and the biological information acquirer 3.

In the embodiment, a plurality of second adhesives 42 is arranged spaced apart from each other. Specifically, the plurality of second adhesives 42 is arranged spaced apart from each other along the outer edge part of the biological information acquirer 3 and in such a way as to surround the center part of the biological information acquirer 3, as viewed in a plan view. Also, when an X-axis and a Y-axis intersecting with the center O of the biological information acquirer 3 and orthogonal to each other, as viewed in a plan view, are set, at least one second adhesive 42 is arranged on each side of the X-axis and at least one second adhesive 42 is arranged on each side of the Y-axis. However, the number and arrangement of the second adhesives 42 are not particularly limited. For example, only one second adhesive 42 may be arranged, or a plurality of second adhesives 42 may be unevenly distributed with respect to the biological information acquirer 3.

Since the hard first adhesive 41 is arranged closely to the center O and the soft second adhesive 42 is arranged on the outer edge side in this manner, the adhesive layer 4 is more deformable at the outer edge part than at the center part. Therefore, the biological information acquirer 3 can change attitude with respect to the rigid substrate 22 similarly to seesaw swings, with the center part of the biological information acquirer 3 acting as the fulcrum, as shown in FIGS. 5 and 6. Thus, the ability of the biological information acquirer 3 to follow the surface of the living body H when the electronic apparatus 1 is installed on the living body H can be improved. Particularly, since the plurality of second adhesives 42 is arranged surrounding the center O of the biological information acquirer 3 as described above, the biological information acquirer 3 can change attitude with respect to the rigid substrate 22 similarly to seesaw swings in any direction (three-dimensionally). Therefore, the ability of the biological information acquirer 3 to follow the surface of the living body H when the electronic apparatus 1 is installed on the living body H can be improved further.

The first adhesive 41 and the second adhesive 42 are not particularly limited, provided that the first adhesive 41 is harder than the second adhesive 42, that is, provided that the elastic modulus of the first adhesive 41 is higher than the elastic modulus of the second adhesive 42. For example, it is preferable that, on the hardness scale of pencils, the first adhesive 41 is below 3 B whereas the second adhesive 42 is 3 B or above. Moreover, it is preferable that the first adhesive 41 and the second adhesive 42 are apart from each other by one level or more on the hardness scale of pencils (for example, if the first adhesive 41 is HB on the hardness scale of pencils, the second adhesive 42 is B or above). With such hardness of the first and second adhesives 41, 42, the biological information acquirer 3 can more easily change attitude as described above and the ability of the biological information acquirer 3 to follow the surface of the living body H is improved further.

In the embodiment, each second adhesive 42 is electrically conductive, and the biological information acquirer 3 is electrically connected to the base 2 by the second adhesives 42. Specifically, as shown in FIGS. 3 and 4, each second adhesive 42 is in contact with a predetermined connection pad 39 and wire 61 arranged on the back side of the biological information acquirer 3. Thus, the electrode pads 51, 52 and the biological information acquirer 3 can be electrically connected to each other by the plurality of second adhesives 42. Since the second adhesives 42 are provided with electrical conductivity, the second adhesives 42 can be used as a part of the electrical path for electrically connecting the electrode pads 51, 52 and the biological information acquirer 3. Therefore, compared with the case where members (for example, lead wires) for electrically connecting the wires 61 and the connection pads 39 are arranged separately from the second adhesives 42, the configuration of the electronic apparatus 1 can be simplified and the electronic apparatus 1 can be miniaturized. Also, since the plurality of second adhesives 42 is provided, a plurality of electrical paths can be formed and the electrical connection between the electrode pads 51, 52 and the biological information acquirer 3 can be achieved more securely.

The second adhesives 42 are made of the same material as the wires 61 and unified with the wires 61. Therefore, the second adhesives 42 and the wires 61 can be formed simultaneously, thus making it easier to manufacture the electronic apparatus 1. However, the second adhesives 42 may be formed separately from the wires 61.

All of the second adhesives 42 may be used for the electrical connection between the electrode pads 51, 52 and the biological information acquirer 3. However, it is also possible that only a part of the second adhesives 42 is used for the electrical connection between the electrode pads 51, 52 and the biological information acquirer 3. In this case, the second adhesives 42 which are not used for the electrical connection between the electrode pads 51, 52 and the biological information acquirer 3 need not be conductive. Also, it is possible that none of the second adhesives 42 is used for the electrical connection between the electrode pads 51, 52 and the biological information acquirer 3. In this case, for example, the biological information acquirer 3 and the wires 61 may be electrically connected to each other with lead wires, and each second adhesive 42 need not be conductive.

Meanwhile, the first adhesive 41 has an insulation property. Thus, electrical connection between the second adhesives 42 via the first adhesive 41 (that is, forming a short circuit) can be restrained effectively.

It is preferable that the first adhesive 41 or the second adhesive 42 includes air bubbles inside. Thus, the flexibility of the first adhesive 41 or the second adhesive 42 (adhesive including air bubbles) increases and therefore the first adhesive 41 or the second adhesive 42 can be deformed more easily. The ability of the biological information acquirer 3 to follow the surface of the living body H when the electronic apparatus 1 is installed on the living body H is improved further. Of the first adhesive 41 and the second adhesive 42, it is preferable that particularly the first adhesive 41 includes air bubbles. Thus, the foregoing effect becomes more prominent.

Up to this point, the first adhesive 41 and the second adhesive 42 have been described. The first adhesive 41 and the second adhesive 42 are not particularly limited. For example, various resin-based adhesives such as epoxy-based resin, acrylic-based resin, urethane-based resin or silicone-based resin, various rubber-based adhesives such as acrylic-based rubber, silicone-based rubber, butadiene-based rubber or styrene-based rubber, or thermoplastic elastomer or the like can be used. Also, adding a cellulose nanofiber, carbon nanofiber or the like reinforces the resin and can provide material strength. To provide the second adhesive 42 with conductivity, the foregoing various resin-based adhesives mixed with various conductive fillers such as metal-based filler (for example, Au, Ag, Cu, Ni, Zn, Al), metal oxide-based filler (for example, $SnO_2$/Sb doped, $In_2O_3$/Sn doped, ZnO/Al doped), or carbon-based filler (for example, conductive carbon black, graphite) can be used.

The method for differentiating the flexibilities of the first adhesive 41 and the second adhesive 42 is not particularly limited. For example, different kinds of materials may be used, or the same material may be used with different amounts of additives added. In the former case, an epoxy-based or acrylic-based adhesive, which is relatively hard, may be used as the first adhesive 41, and a urethane-based or silicone-based adhesive, which is relatively soft, may be used as the second adhesive 42. Also, the hardness of the adhesives may be adjusted by adding a cellulose nanofiber, carbon nanofiber or the like.

The thickness of the adhesive layer 4 is not particularly limited. However, it is preferable that its thickness is 10 μm or more and 1000 μm or less. Providing the adhesive layer 4 with such a thickness enables prevention of an excessive thickness of the adhesive layer 4 and sufficient achievement of the foregoing effects of the adhesive layer 4.

The first adhesive 41 has no gradient of the elastic modulus in the planar direction (direction orthogonal to the direction in which the rigid substrate 22 and the biological information acquirer 3 are arrayed) and has substantially the same elastic modulus over the entire area. The same applies to the second adhesive 42. As a modification of the embodiment, at least one of the first adhesive 41 and the second adhesive 42 may have a gradient of the elastic modulus in the planar direction. That is, at least one of the first adhesive 41 and the second adhesive 42 may have an area where the elastic modulus varies in the planar direction. For example, the elastic modulus of the first adhesive 41 may gradually decrease as it goes toward the outer edge part from the center O of the biological information acquirer 3. Also, the first adhesive 41 may have a center part situated at the center part of the biological information acquirer 3 as viewed in a plane view, and a peripheral part situated to surround this center part, and the elastic modulus of the center part may be higher than the elastic modulus of the peripheral part. Again, with such a configuration, the biological information acquirer 3 can change attitude more easily with respect to the rigid substrate 22 and the ability of the biological information acquirer 3 to follow the surface of the living body H when the electronic apparatus 1 is installed on the living body H is improved.

Second Embodiment

Figure 7:
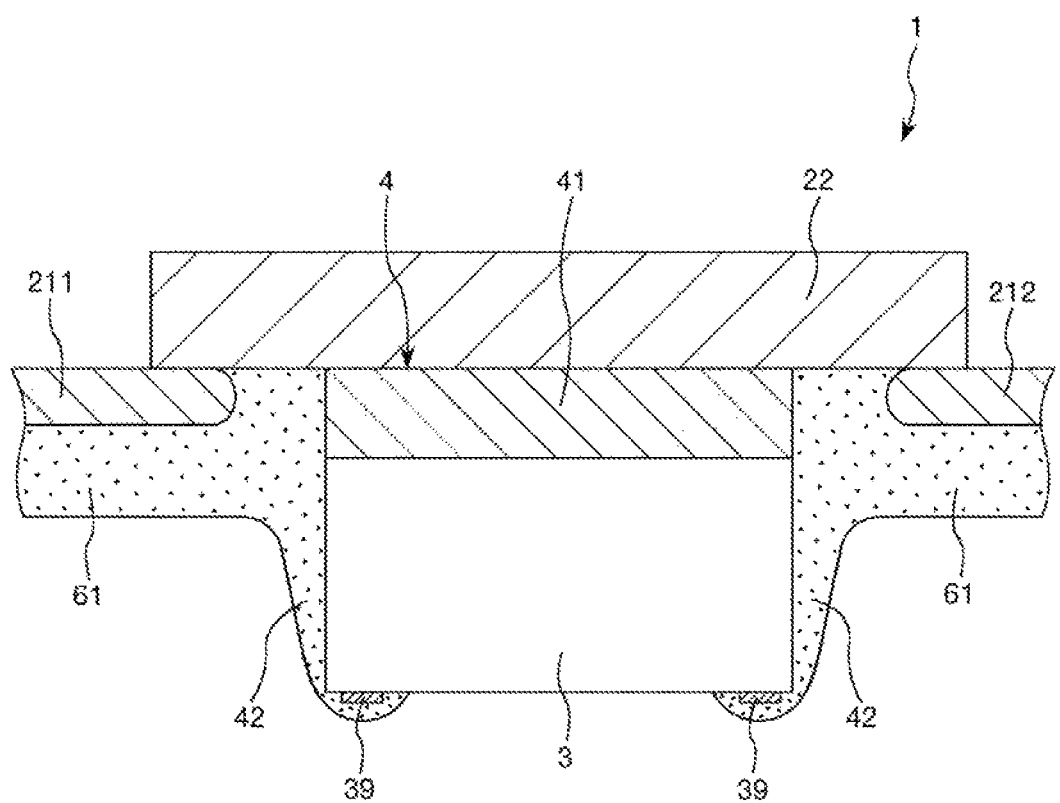
FIG. 7 is a cross-sectional view of an electronic apparatus according to a second embodiment of the invention.

FIG. 7 is a cross-sectional view of an electronic apparatus according to a second embodiment of the invention.

This embodiment is similar to the first embodiment except that the configuration of the adhesive layer is different.

The description below focuses mainly on the difference between this embodiment and the foregoing embodiment. Similar matters will not be described further. In FIG. 7, configurations similar to those in the foregoing embodiment are denoted by the same reference signs.

As shown in FIG. 7, in the electronic apparatus 1 in this embodiment, the first adhesive 41 is provided between the rigid substrate 22 and the biological information acquirer 3, and the second adhesive 42 is provided around the biological information acquirer 3. Specifically, the first adhesive 41 is arranged in such a way as to fill the entire space between the rigid substrate 22 and the biological information acquirer 3. The second adhesive 42 is arranged from the surface of the biological information acquirer 3 to the rigid substrate 22 via the lateral surface of the first adhesive 41. The second adhesive 42 is in contact with the connection pads 39 arranged on the surface of the biological information acquirer 3 and with the wires 61 arranged on the rigid substrate 22 and thus electrically connects the biological information acquirer 3 and the wires 61 to each other.

The second embodiment as described above can achieve effects similar to those of the first embodiment.

Third Embodiment

Figure 8:
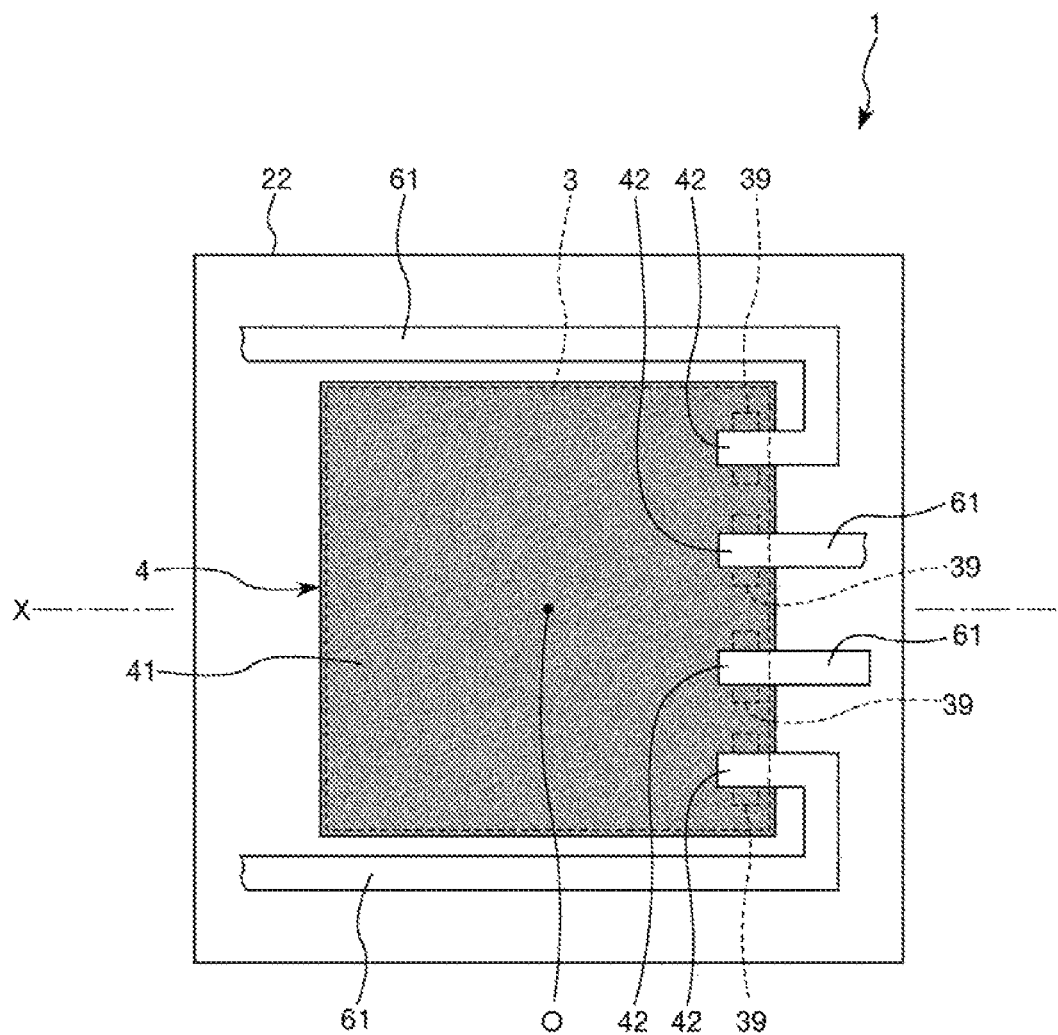
FIG. 8 is a plan view of an electronic apparatus according to a third embodiment of the invention.
Figure 9:
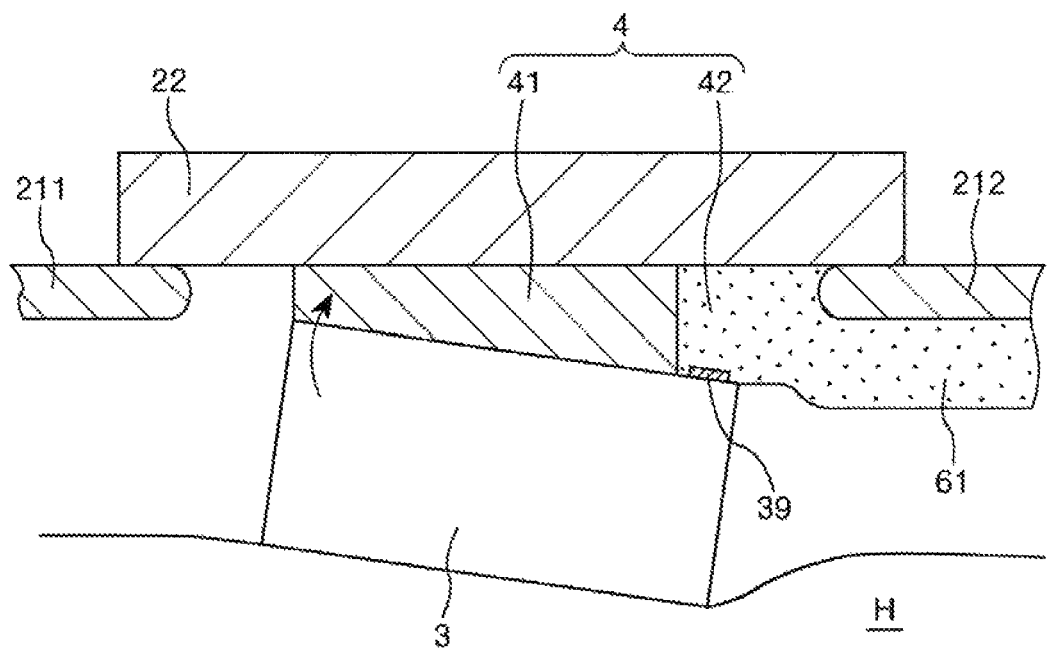
FIG. 9 is a cross-sectional view showing the displacement of a biological information acquirer with respect to a rigid substrate.

FIG. 8 is a plan view of an electronic apparatus according to a third embodiment of the invention. FIG. 9 is a cross-sectional view showing displacement of the biological information acquirer with respect to the rigid substrate.

This embodiment is similar to the first embodiment except that the configuration of the adhesive layer is different.

The description below focuses mainly on the difference between this embodiment and the foregoing embodiment. Similar matters will not be described further. In FIG. 8, configurations similar to those in the foregoing embodiment are denoted by the same reference signs.

As shown in FIG. 8, in the electronic apparatus 1 in this embodiment, all of the second adhesives 42 are arranged, unevenly distributed to one end part of the biological information acquirer 3, as viewed in a plan view. In other words, all of the second adhesives 42 are situated, unevenly distributed into an area of the entire circumference of the outer edge part of the biological information acquirer 3, as viewed in a plan view. More specifically, all of the second adhesives 42 are situated in such away as to overlap the outer edge part on one side in the X-axis direction of the biological information acquirer 3 and are arrayed along the outer edge part, as viewed in a plan view. Moreover, in this embodiment, in contrast to the first embodiment, the second adhesives 42 are harder than the first adhesive 41. That is, the second adhesives 42 have a higher elastic modulus than the first adhesive 41.

Since the second adhesives 42 harder than the first adhesive 41 are thus unevenly distributed to the outer edge side, the biological information acquirer 3 change attitude with respect to the rigid substrate 22 similarly to seesaw swings with the outer edge part of the biological information acquirer 3 (area to which the second adhesive 42 are unevenly distributed) acting as the fulcrum, as shown in FIG. 9. Therefore, the ability of the biological information acquirer 3 to follow the surface of the living body H when the electronic apparatus 1 is installed on the living body H is improved.

The third embodiment as described above can achieve effects similar to those of the first embodiment.

Fourth Embodiment

Figure 10:
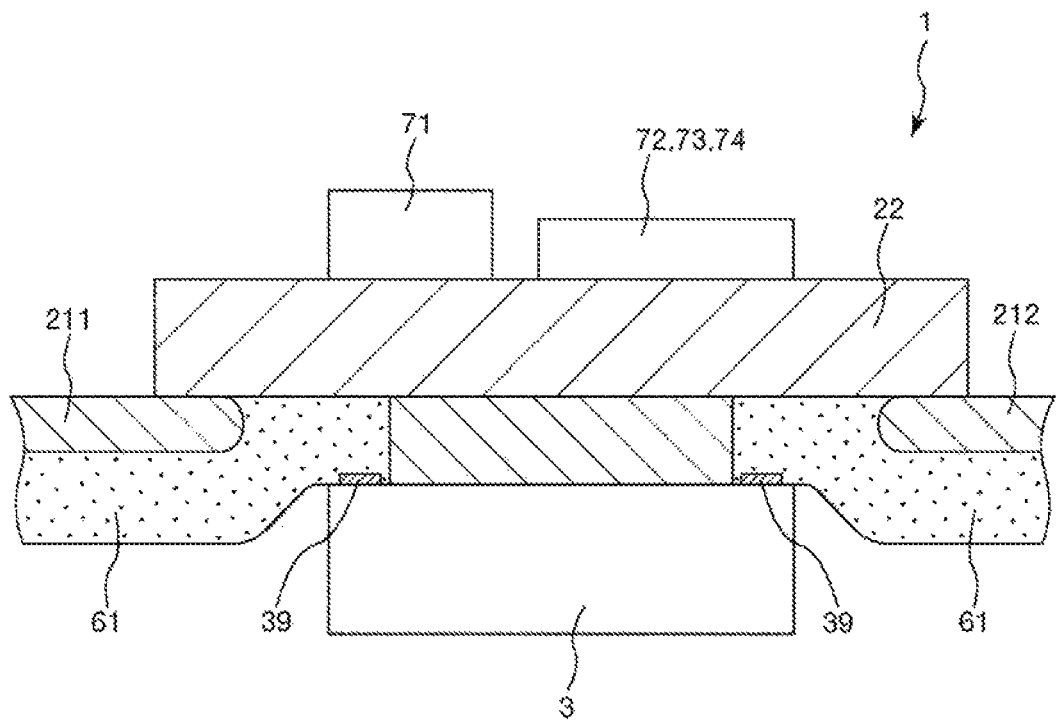
FIG. 10 is a cross-sectional view of an electronic apparatus according to a fourth embodiment of the invention.

FIG. 10 is a cross-sectional view of an electronic apparatus according to a fourth embodiment of the invention.

This embodiment is similar to the first embodiment except that the battery and the IC are provided as separate bodies from the biological information acquirer.

The description below focuses mainly on the difference between this embodiment and the foregoing embodiment.

Similar matters will not be described further. In FIG. 10, configurations similar to those in the foregoing embodiment are denoted by the same reference signs.

As shown in FIG. 10, in the electronic apparatus 1 in this embodiment, the battery 71 and the IC 72 are separate bodies from the biological information acquirer 3 and are arranged on the back side of the rigid substrate 22 (side opposite to the side where the biological information acquirer 3 is arranged). Therefore, the battery 71 and the IC 72 are provided opposite the biological information acquirer 3 via the rigid substrate 22. The battery 71, the IC 72, and the biological information acquirer 3 are electrically connected to each other via wires provided in the rigid substrate 22 (internal wires, not illustrated, and terminals situated on the surface of the rigid substrate 22, or the like) and the second adhesives 42.

Since the battery 71, the IC 72, the storage 73, and the communicator 74 are thus arranged as separate bodies from the biological information acquirer 3, the biological information acquirer 3 can be miniaturized and the biological information acquirer 3 can be brought into tighter contact with the surface of the living body H. Particularly, since the battery 71, the IC 72, the storage 73, and the communicator 74 are arranged on the back side of the rigid substrate 22, both sides of the rigid substrate 22 can be effectively utilized.

The fourth embodiment as described above can achieve effects similar to those of the first embodiment.

Fifth Embodiment

Figure 11:
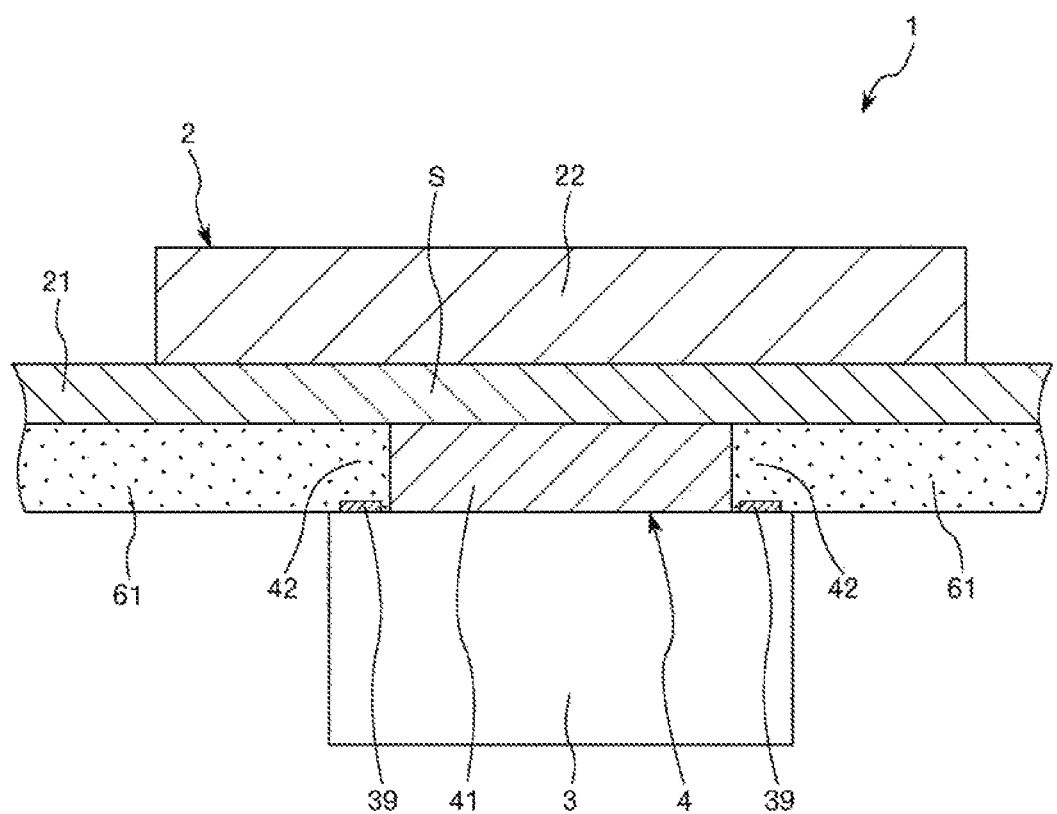
FIG. 11 is a cross-sectional view of an electronic apparatus according to a fifth embodiment of the invention.

FIG. 11 is a cross-sectional view of an electronic apparatus according to a fifth embodiment of the invention.

This embodiment is similar to the first embodiment except that the configuration of the base is different.

The description below focuses mainly on the difference between this embodiment and the foregoing embodiment. Similar matters will not be described further. In FIG. 11, configurations similar to those in the foregoing embodiment are denoted by the same reference signs.

As shown in FIG. 11, the base 2 in this embodiment has a strap 21 and a rigid substrate 22 joined to the strap 21 in such a way as to overlap a center part of the strap 21. The strap 21 is not divided into two strap pieces as in the first embodiment and is formed by one long member. When the area of the strap 21 joined to the rigid substrate 22 (area overlapping with the rigid substrate 22, as viewed in a plan view) is defined as an area S, the biological information acquirer 3 is joined to the strap 21 via the adhesive layer 4 (first adhesive 41 and second adhesive 42) in this area S. In the area S, the strap 21 is joined to the rigid substrate 22 and therefore the deformation of the strap 21 is regulated by the rigid substrate 22. Thus, again, with such a configuration, the joining surface between the strap 21 and the adhesive layer 4 can be maintained in good condition and the separation of the adhesive layer 4 from the strap 21 can be restrained effectively, as in the first embodiment.

The fifth embodiment as described above can achieve effects similar to those of the first embodiment.

Sixth Embodiment

Figure 12:
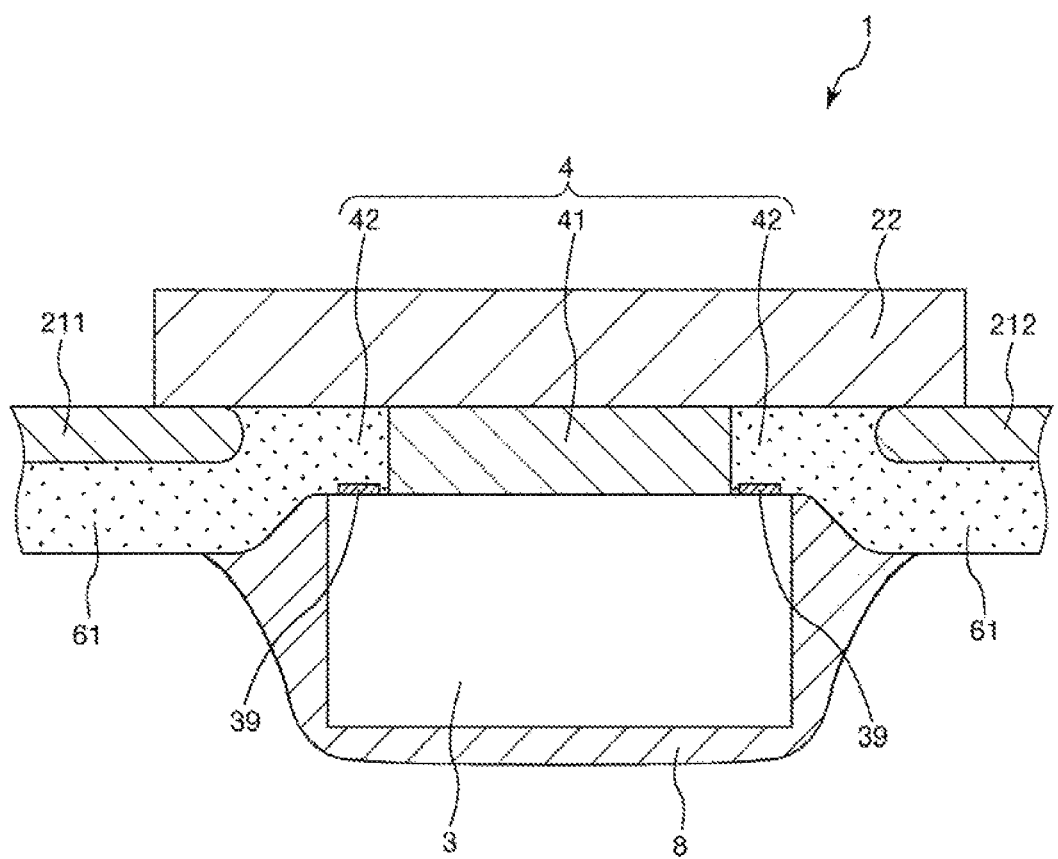
FIG. 12 is a cross-sectional view of an electronic apparatus according to a sixth embodiment of the invention.
Figure 13:
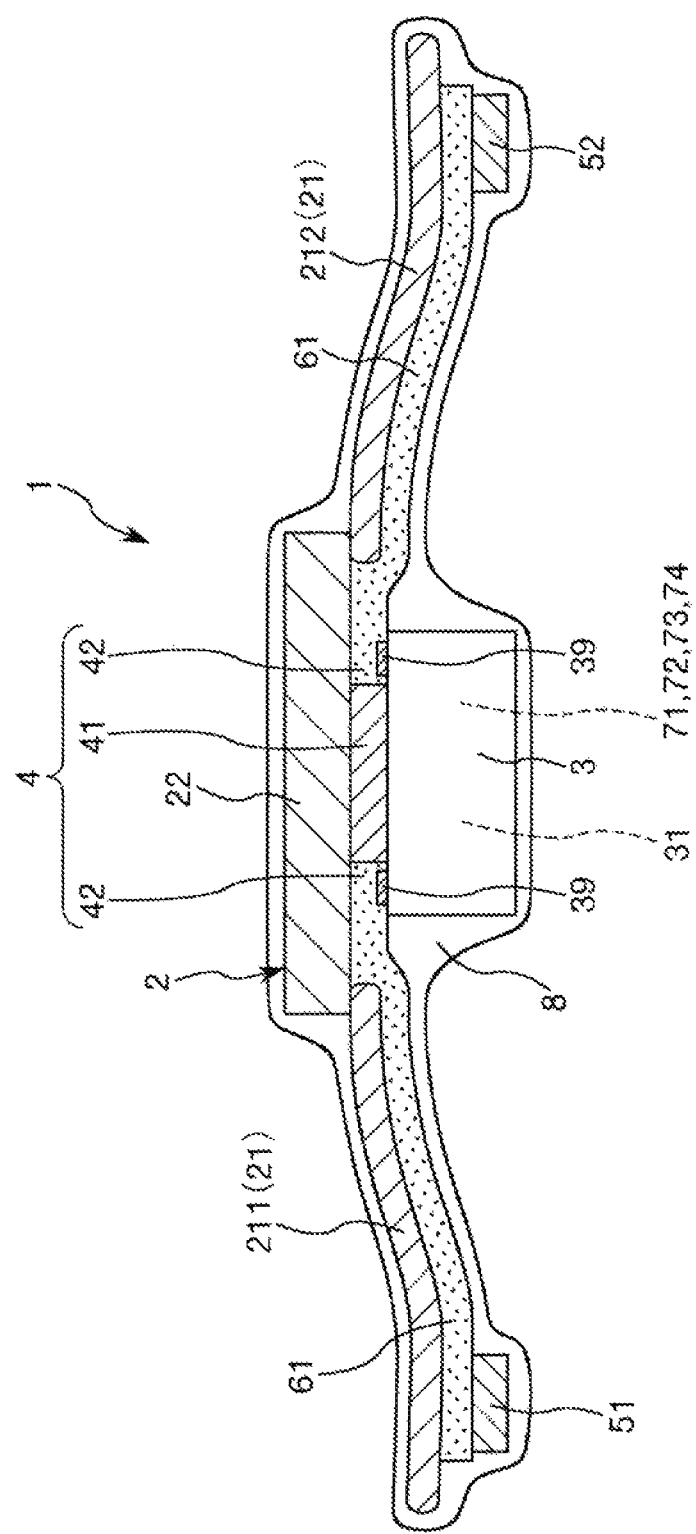
FIG. 13 is a cross-sectional view showing a modification of the electronic apparatus shown in FIG. 12.

FIG. 12 is a cross-sectional view of an electronic apparatus according to a sixth embodiment of the invention. FIG. 13 is cross-sectional view showing a modification of the electronic apparatus shown in FIG. 12.

This embodiment is similar to the first embodiment except that the configuration of the base is different.

The description below focuses mainly on the difference between this embodiment and the foregoing embodiment. Similar matters will not be described further. In FIG. 12, configurations similar to those in the foregoing embodiment are denoted by the same reference signs.

As shown in FIG. 12, the electronic apparatus 1 in this embodiment has a coating 8 as a third member which has elasticity and is arranged in such a way as to cover at least a part of the peripheries of the biological information acquirer 3, as viewed in a plan view (plan view taken from the direction in which the base 2 and the biological information acquirer 3 are arrayed). Particularly, the coating 8 in this embodiment is provided to cover the entire circumference of the biological information acquirer 3 and the adhesive layer 4. The provision of such a coating 8 enables projection of the biological information acquirer 3 and the adhesive layer 4 from impacts and duct and thus enables reduction in the possibility of malfunction of the electronic apparatus 1. Here, it is preferable that the coating 8 is damp-proof. This can enables further protection of biological information acquirer 3 and the adhesive layer 4 from moisture. The arrangement of the coating 8 is not particularly limited, provided that the coating 8 covers at least a part of the peripheries of the biological information acquirer 3, as viewed in a plan view. For example, it is possible that the coating 8 does not cover the top surface (surface on the side of the living body H) of the biological information acquirer 3. That is, the top surface of the biological information acquirer 3 may be exposed from the coating 8.

The elastic modulus of the coating 8 is lower than the elastic modulus of the second adhesive 42. As the coating 8 is thus made more flexible than the second adhesive 42, the coating 8 can be restrained from making it difficult for the biological information acquirer 3 to change attitude with respect to the rigid substrate 22. Therefore, a high ability of the biological information acquirer 3 to follow the surface of the living body H can be maintained and the advantages of the coating 8 can be achieved.

The coating 8 is not particularly limited, provided that the coating 8 is more flexible than the second adhesive 42, that is, provided that the elastic modulus of the coating 8 is lower than the elastic modulus of the second adhesive 42. For example, as described above, it is preferable that the hardness of the second adhesive 42 is below 6 B on the hardness scale of pencils. Therefore, it is preferable that the hardness of the coating 8 is below 9 B, which is even softer. With the provision of the coating 8 with such hardness, the foregoing advantages can be achieved more suitably.

The material of the coating 8 is not particularly limited. For example, various resin materials such as epoxy-based resin, urethane-based resin, acrylic-based resin, and silicone-based resin can be used. Of these resin materials, the silicone-based resin is particularly preferable because of its affinity to the living body H.

The sixth embodiment as described above can achieve effects similar to those of the first embodiment. As a modification of this embodiment, the coating 8 may be arranged, covering the entire area of the base 2 and the biological information acquirer 3, for example, as shown in FIG. 13. With such a configuration, the coating 8 can further protect the wires 61 and the electrode pads 51, 52 from impacts, dust, moisture and the like.

Seventh Embodiment

Figure 14:
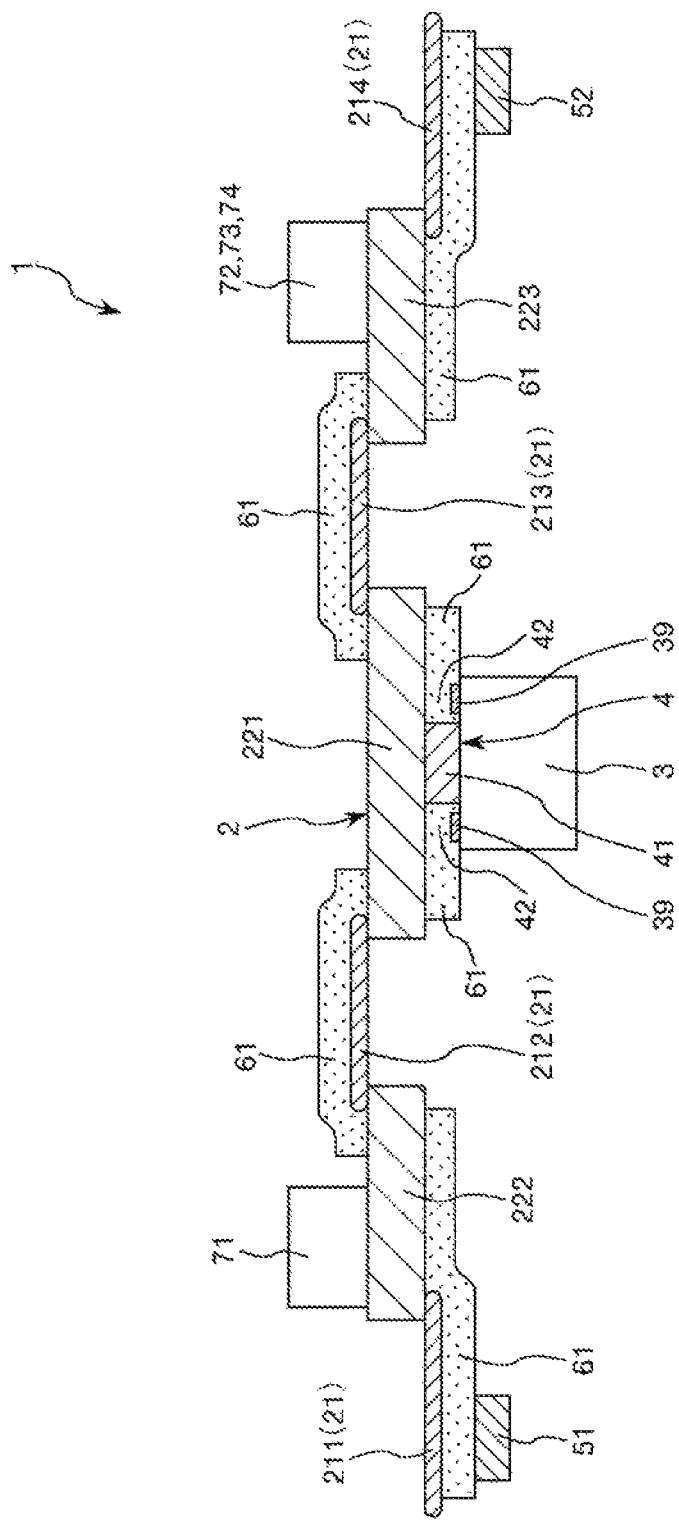
FIG. 14 is a cross-sectional view of an electronic apparatus according to a seventh embodiment of the invention.

FIG. 14 is a cross-sectional view of an electronic apparatus according to a seventh embodiment of the invention.

This embodiment is similar to the first embodiment except that the configuration of the base is different.

The description below focuses mainly on the difference between this embodiment and the foregoing embodiment. Similar matters will not be described further. In FIG. 14, configurations similar to those in the foregoing embodiment are denoted by the same reference signs.

As shown in FIG. 14, in the electronic apparatus 1 in this embodiment, the base 2 has three rigid substrates 221, 222, 223 arranged spaced apart from each other. The biological information acquirer 3 is arranged on the rigid substrate 222 situated in the middle. The battery 71 is arranged on the rigid substrate 221 situated on one side of the rigid substrate 222. The IC 72, the storage 73, and the communicator 74 are arranged on the rigid substrate 223 situated on the other side. With such an arrangement, the biological information acquirer 3, the battery 71, and the IC 72 can be spaced further apart from each other than, for example, in the first and fourth embodiments. Therefore, a signal acquired by the biological information acquirer 3 is not easily affected by a noise. Thus, accurate biological information can be acquired.

The strap 21 includes a strap piece 211 situated more closely to the edge than the rigid substrate 221 and having one end connected to the rigid substrate 221, a strap piece 212 situated between the rigid substrates 221, 222 and connecting these, a strap piece 213 situated between the rigid substrates 221, 223 and connecting these, and a strap piece 214 situated more closely to the edge than the rigid substrate 223 and having one end connected to the rigid substrate 223. The electrode pad 51 is arranged on the strap piece 211. The electrode pad 52 is arranged on the strap piece 214.

On the base 2 of such a configuration, a plurality of wires 61 is provided. The biological information acquirer 3, the battery 71, the IC 72, and the electrode pads 51, 52 are electrically connected via these wires 61. An internal wire, not illustrated, is provided in each of the rigid substrates 221, 222, 223. The wires 61 situated on the top side and wires situated on the bottom side are electrically connected via the internal wires.

The seventh embodiment as described above can achieve effects similar to those of the first embodiment. Although the base 2 in this embodiment has three rigid substrates, the number of rigid substrates is not particularly limited.

The electronic apparatus according to the invention has been described, based on the illustrated embodiments. However, the invention is not limited to these embodiments. The configuration of each component can be replaced by an arbitrary configuration having similar functions. Also, other arbitrary components may be added to the invention. The individual embodiments may be suitably combined.

In the above embodiments, a configuration in which the bonding element provided on the base so that the electronic apparatus can be fastened to the living body by having this bonding element bonded to the living body is described. However, the method for fastening the electronic apparatus to the living body is not particularly limited. For example, the electronic apparatus may be able to be fastened to the living body by having the strap wound around an arm or the like of the living body. Alternatively, the electronic apparatus itself may be without any bonding element, and the electronic apparatus may be able to be fastened to the living body, using a bonding member such as an adhesive tape or the like.

In the above embodiments, a configuration in which the electronic apparatus is applied to a wearable terminal is described. However, the electronic device is not limited to the wearable terminal. Also, though a configuration using the biological information acquirer for acquiring biological information as a functional element is described, the configuration of the functional element is not particularly limited. For example, a medicator capable of giving a percutaneous medication at predetermined time (for example, a configuration in which a puncture needle protrudes and is inserted into a living body at predetermined time so as to medicate a drug solution such as insulin from the puncture needle) may be employed.

In the above embodiments, a configuration in which the electronic apparatus is used on a human is described. However, the target on which the electronic apparatus is used is not limited to a living body and may be, for example, a corpse, or may be animals, insects and the like other than humans, and plants. The electronic apparatus may also be used on various artificial objects other than organisms.

In the above embodiments, a configuration in which the elastic modulus of the first adhesive is higher than the elastic modulus of the second adhesive is described. However, the elastic modulus of the first adhesive and the elastic modulus of the second adhesive are not particularly limited, provided that these elastic moduli are different from each other. Also, though a configuration in which the base has a rigid substrate (hard member) and a strap (flexible member) is described in the above embodiments, the configuration of the base is not particularly limited. For example, the base may be made up of a flexible member or made up of a hard member.

The entire disclosure of Japanese Patent Application No. 2016-178570 filed on Sep. 13, 2016 is expressly incorporated by reference herein.

What is claimed is:

1. A wearable biological information sensing device comprising:
 a base having first and second surfaces and first and second sides;
 a wrist band connected to the first and second sides of the base to be worn on a wrist of a user;
 a first adhesive disposed at a center area of the second surface of the base;
 a second adhesive disposed at a periphery of the second surface of the base, the second adhesive surrounding the first adhesive in a plan view; and
 a biological information acquisition sensor configured to acquire biological information of the user from the wrist, the biological information acquisition sensor being disposed on a plane of the first and second adhesives so that the first and second adhesives are directly sandwiched by the base and the biological information acquisition sensor,
 wherein the first adhesive has a first elastic modulus, the second adhesive has a second elastic modulus, and the first elastic modulus of the first adhesive is higher than the second elastic modulus of the second adhesive.

2. The wearable biological information sensing device according to claim 1, wherein
 at least one of the first elastic modulus or the second elastic modulus has a gradient elastic modulus.

3. The wearable biological information sensing device according to claim 1, further comprising:
 a coating which has elasticity and is arranged to cover a periphery of the biological information acquisition sensor in the plan view.

4. The wearable biological information sensing device according to claim 3, wherein the coating has a third elastic modulus that is lower than the second elastic modulus of the second adhesive.

5. The wearable biological information sensing device according to claim 1, wherein the second adhesive has electrical conductivity, and
the biological information acquisition sensor is electrically connected to the base via the second adhesive.

6. The wearable biological information sensing device according to claim 1, wherein the second adhesive is configured by a plurality of second adhesives that are spaced apart from each other.

7. The wearable biological information sensing device according to claim 1, wherein the first adhesive has an insulation property.

8. The wearable biological information sensing device according to claim 1, wherein one of the first adhesive or the second adhesive includes air bubbles therein.

* * * * *